(12) United States Patent
Kliesch et al.

(10) Patent No.: US 7,960,010 B2
(45) Date of Patent: Jun. 14, 2011

(54) ANTIMICROBIALLY MODIFIED, BIAXIALLY ORIENTED POLYESTER FILM

(75) Inventors: Holger Kliesch, Ginsheim-Gustavsburg (DE); Bodo Kuhmann, Runkel (DE); Ingo Fischer, Heistenbach (DE); Lothar Bothe, Mainz (DE); Matthias Konrad, Hofheim (DE)

(73) Assignee: Mitsubishi Polyester Film GmbH, Wiesbaden (DE)

( * ) Notice: Subject to any disclaimer, the term of this patent is extended or adjusted under 35 U.S.C. 154(b) by 0 days.

(21) Appl. No.: 12/269,284

(22) Filed: Nov. 12, 2008

(65) Prior Publication Data

US 2009/0123723 A1    May 14, 2009

(30) Foreign Application Priority Data

Nov. 14, 2007    (DE) .................. 10 2007 054 132

(51) Int. Cl.
     *B32B 27/06*      (2006.01)
     *B32B 27/18*      (2006.01)
     *B32B 27/20*      (2006.01)
     *B32B 27/36*      (2006.01)
     *B32B 37/15*      (2006.01)

(52) U.S. Cl. ........ 428/141; 428/212; 428/323; 428/328; 428/334; 428/336; 428/339; 428/480; 428/910; 523/122; 106/15.05; 524/450; 264/173.17; 264/280; 264/288.4; 264/290.2

(58) Field of Classification Search .................. None
See application file for complete search history.

(56) References Cited

U.S. PATENT DOCUMENTS

| | | | | |
|---|---|---|---|---|
| 4,911,898 A * | 3/1990 | Hagiwara et al. | ............ | 423/700 |
| 4,938,958 A * | 7/1990 | Niira et al. | ............ | 424/78.1 |
| 5,556,699 A * | 9/1996 | Niira et al. | ............ | 428/323 |
| 5,844,022 A * | 12/1998 | Nishioka et al. | ............ | 523/218 |
| 6,013,275 A * | 1/2000 | Konagaya et al. | ............ | 424/443 |
| 6,114,021 A * | 9/2000 | Pankratz et al. | ............ | 428/214 |
| 6,150,004 A * | 11/2000 | Oikawa et al. | ............ | 428/141 |
| 6,358,604 B1 * | 3/2002 | Peiffer et al. | ............ | 428/336 |
| 6,458,467 B1 * | 10/2002 | Mizuno et al. | ............ | 428/480 |
| 6,607,808 B2 * | 8/2003 | Peiffer et al. | ............ | 428/141 |
| 6,627,695 B2 * | 9/2003 | Murschall et al. | ............ | 524/513 |
| 6,723,428 B1 * | 4/2004 | Foss et al. | ............ | 428/370 |
| 6,855,758 B2 * | 2/2005 | Murschall et al. | ............ | 524/195 |
| 6,863,954 B2 * | 3/2005 | Peiffer et al. | ............ | 428/141 |
| 6,872,460 B2 * | 3/2005 | Murschall et al. | ............ | 428/480 |
| 6,902,818 B2 * | 6/2005 | Murschall et al. | ............ | 428/480 |
| 7,026,035 B2 * | 4/2006 | Yano et al. | ............ | 428/141 |
| 7,041,723 B2 * | 5/2006 | Kimura | ............ | 524/413 |
| 7,063,889 B2 * | 6/2006 | Yoshida et al. | ............ | 428/327 |
| 2003/0091767 A1 * | 5/2003 | Podhajny | ............ | 428/35.7 |
| 2003/0235703 A1 * | 12/2003 | Kliesch et al. | ............ | 428/480 |
| 2004/0147654 A1 * | 7/2004 | Kimura | ............ | 524/403 |
| 2004/0156918 A1 * | 8/2004 | Podhajny | ............ | 424/618 |
| 2005/0079372 A1 * | 4/2005 | Schmal et al. | ............ | 428/482 |
| 2005/0100574 A1 * | 5/2005 | Furukawa et al. | ............ | 424/405 |
| 2006/0222845 A1 * | 10/2006 | Deng et al. | ............ | 428/336 |
| 2007/0110825 A1 * | 5/2007 | Taniguchi et al. | ............ | 424/618 |
| 2010/0247889 A1 * | 9/2010 | Kliesch et al. | ............ | 428/220 |

FOREIGN PATENT DOCUMENTS

| | | | |
|---|---|---|---|
| DE | 10100704 | * | 7/2002 |
| EP | 0 031 202 A2 | | 7/1981 |
| EP | 0 031 203 A2 | | 7/1981 |
| EP | 0 076 582 A1 | | 4/1983 |
| EP | 0 116 865 A1 | | 8/1984 |
| EP | 0 144 878 B1 | | 6/1985 |
| EP | 0 144 948 B2 | | 6/1985 |
| EP | 0 288 063 A2 | | 10/1988 |
| EP | 0 297 538 A2 | | 1/1989 |
| EP | 1 165 317 | | 8/2000 |
| EP | 1 097 809 A1 | | 5/2001 |
| EP | 1 138 480 A2 | | 10/2001 |
| EP | 1 471 098 | | 10/2004 |
| FR | 2 811 304 A2 | | 11/2002 |
| JP | 62 195038 | | 8/1987 |
| JP | 09-057922 | * | 3/1997 |
| JP | 09 057923 | | 3/1997 |
| JP | 09057922 | | 3/1997 |
| JP | 10-086290 | * | 4/1998 |
| JP | 10-086290 | * | 7/1998 |
| JP | 11193358 A | | 10/1998 |
| WO | WO 98/06575 A1 | | 2/1998 |
| WO | WO 00/30697 A1 | | 6/2000 |
| WO | WO 02/062577 A1 | | 8/2002 |
| WO | WO 2006/000755 A2 | | 1/2006 |
| WO | WO 2006/102858 A2 | | 10/2006 |
| WO | WO 2006/102957 A2 | | 10/2006 |
| WO | WO 2008/151948 A2 | | 12/2008 |

* cited by examiner

*Primary Examiner* — Vivian Chen
(74) *Attorney, Agent, or Firm* — ProPat, L.L.C.

(57) ABSTRACT

The invention relates to a multilayer, antimicrobially modified, biaxially oriented polyester film that includes at least one base layer (B) and an outer layer (A) that has been applied to the base layer and that has also been antimicrobially modified, wherein the antimicrobially modified outer layer (A) comprises a silver-loaded zeolite, has a layer thickness <8 μm, and the layer thickness is not greater than 1.3 times the median particle size of the zeolite. The invention further relates to a process for the production of the film, and to the use of the film.

19 Claims, No Drawings

ANTIMICROBIALLY MODIFIED, BIAXIALLY ORIENTED POLYESTER FILM

CROSS-REFERENCE TO RELATED APPLICATIONS

This application claims priority to German Patent Application No. 10 2007 054 132.7 filed Nov. 14, 2007 which is hereby incorporated herein by reference in its entirety.

FIELD OF THE INVENTION

The invention relates to a multilayer, antimicrobially modified, biaxially oriented polyester film, comprised of at least one base layer (B) and of an outer layer (A) which has been applied to this base layer and which has been antimicrobially modified. The invention further relates to a process for the production of the film, and to the use of the film.

The films of the invention, and items produced therefrom, are particularly suitable for use in medical equipment and packaging, walls of cold stores (e.g. as laminate on steel), surfaces in large-scale kitchens, hospitals, etc. The films particularly have very good suitability for the covering and therefore the protection of metallic surfaces, to which the films are heat-sealed or are laminated using adhesives.

BACKGROUND OF THE INVENTION

Antimicrobially modified, biaxially oriented polyester films are known.

WO 2002/062577 describes polyester films anti-microbially modified using triclosan. The migration of triclosan from PET is very slow, however, and effective antimicrobial action is therefore possible only with high loadings. Triclosan is moreover a chlorinated organic compound, which can react further during the regrinding process (e.g. of the film edge trims arising in the film production process) to give potentially toxic chlorine compounds. Triclosan is, moreover, undesirable in many applications for environmental reasons and because of the risk of development of resistance.

WO 2006/000755 describes polyester films equipped with a zirconium phosphate comprising silver ions. Because of the layer structure of these phosphates, only small gaps are available for escape of the silver, and this likewise means that relatively high loadings are necessary for effective defense from microorganisms.

U.S. Pat. No. 5,556,699 describes polymer films equipped with a zeolite containing silver ions. Although polyesters are mentioned as suitable polymer substrates, no polyester films are described in the Examples. The patent describes suitable zeolites in various sizes, which were introduced into films with different layer structure. The polymers used for the films described moreover also exhibited a fall-off in antimicrobial action at a zeolite particle size in the region of the thickness of the layer equipped with said zeolite.

SUMMARY OF ADVANTAGEOUS EMBODIMENTS OF THE INVENTION

It was an object of the present invention to provide an antimicrobial film which is based on biaxially stretched polyesters and which has an adequate effect at minimum silver loading.

DETAILED DESCRIPTION OF ADVANTAGEOUS EMBODIMENTS OF THE INVENTION

The foregoing object is achieved via an at least two-layer polyester film, which has at least one antimicrobially modified outer layer, where this antimicrobially modified layer has a) from 0.5 to 15% by weight of a silver-loaded zeolite, and
b1) a layer thickness <8 μm, and
b2) this layer thickness is not greater than 1.3 times the median particle size of the zeolite.

The silver in the zeolite here takes the form of silver ions or takes the form of elemental silver, but it is preferable that most (>50% by weight), and particularly preferably all (100% by weight), takes the form of silver ions.

The film of the invention is at least a two-layer film, and comprises the base layer (B), the antimicrobially modified outer layer (A), and, if appropriate, further layers. In the preferred embodiment, the film is a three-layer film. The second outer layer (C) here can likewise have antimicrobial modification, so that unintended reversal of the sides in the end use does not lead to any loss of antimicrobial effectiveness. In another preferred embodiment, the outer layer (C) is sealable, so that the film can be laminated inter alia to steel sheet. Sealable layers are described by way of example in United States Published Application No. 2001/0035593 (whose European equivalent is EP-A-1 138 480), U.S. Pat. No. 6,878,442 (whose European equivalent is EP-A-1 097 809), United States Published Application No. 2005/0074599 (whose European equivalent is EP-A-1 471 098), and EP-A-1 165 317, and are generally comprised of copolyesters. Alongside the base layer and one or two outer layers, further intermediate layers can be present in the film, these preferably not having antimicrobial modification, since this material cannot migrate sufficiently to the surface, and the additional antimicrobial additive does not become effective.

Material for Base Layer (B), Intermediate Layers, and Non-sealable Outer Layers (C):

The layers mentioned of the film are preferably comprised of at least 80% by weight of a thermoplastic polyester. A maximum of 20% by weight of polyamides, polyetherimides, and/or other polymers can be present alongside polyesters. The proportion of these polymers is preferably below 5% by weight and particularly preferably <1% by weight.

Examples of suitable polyesters are those comprised of ethylene glycol and terephthalic acid (=polyethylene terephthalate, PET), of ethylene glycol and naphthalene-2,6-dicarboxylic acid (=polyethylene 2,6-naphthalate, PEN), of 1,4-bishydroxymethylcyclohexane and terephthalic acid (=poly-1,4-cyclohexane-dimethylene terephthalate, PCDT), and also of ethylene glycol, naphthalene-2,6-dicarboxylic acid, and biphenyl-4,4'-dicarboxylic acid (=polyethylene 2,6-naphthalate bibenzoate, PENBB). Preference is given to polyesters which are comprised of at least 60 mol %, particularly preferably at least 80 mol %, of ethylene glycol units and terephthalic acid units. The remaining monomer units derive from other aliphatic, cyclo-aliphatic, or aromatic diols and, respectively, dicarboxylic acids.

Examples of other suitable aliphatic diols are diethylene glycol, triethylene glycol, polyethylene glycol of the general formula HO—$((CH_2)_2$—O)n-$(CH_2)_2$—OH, where n is a number from 3 to 1000, aliphatic glycols of the general formula HO—$(CH_2)_n$—OH, where n is a whole number from 3 to 6 (in particular propane-1,3-diol, butane-1,4-diol, pentane-1,5-diol, and hexane-1,6-diol), or branched aliphatic glycols having up to 6 carbon atoms. Among the cycloaliphatic diols, mention may be made of cyclohexanediols (in particular cyclohexane-1,4-diol). Suitable other aromatic diols correspond by way of example to the formula HO—$C_6H_4$—X—$C_6H_4$—OH, where X is —$CH_2$—, —$C(CH_3)_2$—, —$C(CF_3)_2$—, —O—, —S—, or —$SO_2$—. Bisphenols of the formula HO—$C_6H_4$—$C_6H_4$—OH also have good suitability, but their proportion should not exceed 5% by weight, preferably 1% by weight.

Preferred other aromatic dicarboxylic acids are benzenedicarboxylic acids, naphthalenedicarboxylic acids (such as naphthalene-1,4- or -1,6-dicarboxylic acid), biphenyl-x,x'-dicarboxylic acids (in particular biphenyl-4,4'-dicarboxylic acid), diphenylacetylene-x,x'-dicarboxylic acids (in particular diphenyl-acetylene-4,4'-dicarboxylic acid), or stilbene-x,x'-dicarboxylic acids. Among the cycloaliphatic dicarboxylic acids, mention may be made of cyclohexanedicarboxylic acids (in particular cyclohexane-1,4-dicarboxylic acid). Among the aliphatic dicarboxylic acids, the ($C_3$-$C_{19}$)-alkanediacids are particularly suitable, where the alkane moiety can be straight-chain or branched.

In a thermoformable embodiment, the base-layer polymer is preferably comprised of less than 95 mol % of ethylene glycol units and terephthalic acid units, and particularly preferably of less than 90 mol % of ethylene glycol units and terephthalic acid units.

Polymers for any sealable layer (C) can be found by way of example in the abovementioned EP-A-1 138 480, EP-A-1 097 809, EP-A-1 471 098, EP-A-1 165 317, without any restriction to the blends mentioned in those publications.
Material for Antimicrobially Modified Outer Layer (A), and for any Further Antimicrobially Modified Outer Layer (C) Present:

The polymer for this outer layer in essence corresponds to that for the base layer (B). Here again, preference is given to polyesters which are comprised of at least 60 mol %, and particularly preferably at least 80 mol %, of ethylene glycol units and terephthalic acid units. It has, however, proven advantageous for the polyester to be comprised of less than 99 mol %, and preferably less than 97 mol %, of ethylene glycol units and terephthalic acid units. Although a higher proportion of copolyester facilitates the release of silver ions from the zeolite into the medium situated thereabove, and improves effectiveness, a high proportion of copolyester reduces the level of resistance characteristics of the layer and can, particularly if the surface is cleaned with solvent-containing cleaning compositions (ethanol, acetone, etc.), lead to rapid loss of activity and to alterations in the optical properties of the surface.

The following ranges are therefore preferable:

|  | Preferred (% by wt.) | Particularly preferred (% by wt.) |
|---|---|---|
| Isophthalic acid (IPA) | 1-10 | 4-8 |
| DEG (diethylene glycol) | 1-10 | 1-3 |
| Other diols | 0.7-10 | 1-2 |
| Dicarboxylic acids other than terephthalic acid | 1-10 | 1.5-4 |

The copolyester components can be combined with one another. However, particularly for the above-mentioned reasons, no more than two modification components should be selected; the amounts of the other optional components should then be below the ranges stated as preferred. The amounts of the two components in any combination should moreover not be in the region of the upper limits of the preferred range. If there is more than one comonomer component, the amounts of both ideally lie within the range shown as particularly preferred, and this means that a film with 4% by weight of IPA and 2% by weight of DEG (both within the particularly preferred range) should comprise less than 0.7% by weight of other diols and less than 1% by weight of other carboxylic acids (less than the respective lower limit of the preferred range).

The polyesters can by way of example be prepared by the transesterification process. This starts from dicarboxylic esters and diols, these being reacted with the usual transesterification catalysts, such as salts of zinc, of calcium, of lithium, of sodium, of magnesium, and of manganese. The intermediates are then polycondensed in the presence of well known polycondensation catalysts, such as antimony trioxide or titanium salts. However, they can equally well be prepared by the direct esterification process in the presence of polycondensation catalysts. This process starts directly from the dicarboxylic acids and the diols. Polyesters of the invention are commercially available products.

The concentration of the silver-loaded zeolite added to the outer layer (A) is from 0.5 to 15% by weight. Loadings of from 1 to 6% by weight are preferred here, particular preference being given to a loading of from 1.5 to 3.5% by weight. The higher the loading with zeolite, the greater the impairment of surface quality and of the optical properties of the film, and this means that roughness and haze increase. The haze often impairs the appearance of the finished product (e.g. steel sheet) and is generally undesirable, but exceptions are provided by white films or films involving matt design. High roughness facilitates adhesion of microbes to the surface and is therefore likewise undesirable. The roughness of the surface should generally be below $R_a$=1000 nm, preferably below 600 nm, and particularly preferably below 300 nm.

The median particle size ($d_{50}$) of the zeolites here is generally from 0.5 to 15 µm, preferably from 1.8 to 6 µm, and particularly preferably from 2.1 to 3.5 µm. Although it has been found that smaller zeolites release silver more rapidly and hence that the initial activities can be better with smaller zeolites (<1.8 µm) than with large zeolites, for identical loading and silver concentration in the layer, it has always proven advantageous after a number of cleaning cycles (see description of test methods) to use larger zeolites (>1.8 µm) to ensure that effectiveness is retained. In the case of large zeolites (>6 µm) and in particular in the case of very large zeolites (>15 µm), the distribution at the surface becomes too non-uniform to ensure adequate effectiveness against bacteria. Although this can be compensated by raising the loading, there are resultant disadvantages in cost-effectiveness and in the process performance of the film, since excessive loadings, in particular with large particles, cause an increase in the number of break-offs during film production.

Abrasion during production and during further processing, and also in the end use, also generally increases with the size of the zeolite. This leads not only to dust, which is in any case undesirable, but also to a loss of effectiveness. The range stated above, from 2.1 to 3.5 µm, has therefore proven particularly advantageous.

If the $d_{50}$ value of the size distribution of the zeolite amounts to more than twice the layer thickness of the layer comprising the zeolite, the result for abrasion has generally proven disadvantageous. In some applications which require only short-lived activity (e.g. packaging) it has proven advantageous to add not only the zeolites with particle sizes in the preferred range but also again from 20 to 60% by weight (of the amount of said preferred particles) of zeolites whose particle size is <1.8 µm and ≧0.5 µm.

The amount of silver in the zeolite is preferably from 0.5 to 20% by weight and particularly preferably from 3 to 6% by weight. It has moreover proven advantageous for the zeolite to contain from 1 to 20% by weight of zinc and/or copper. It is preferable that the zeolite contains at least 6% by weight of zinc or/and copper. These zeolites are prepared by known processes as described by way of example in JP 11193358, EPA-0 297 538, or US 2004/147654. Zeolites that can be used in the invention are obtainable by way of example with trade names BACTEKILLER® (Kanebo, JP) or ZEOMIC® (Sinanen, JP).

Alongside the zeolite loading, the ratio of particle size of the zeolite and layer thickness of the layer modified therewith has also proven particularly important. The layer thickness here is from 0.75 to 8 μm and preferably from 1.5 to 5 μm, and particularly preferably from 2 to 2.9 μm. The layer here is no thicker than 1.3 times the median particle size of the zeolite, the dimension preferably being from 0.8 to 1.1 times the median particle size of the zeolite. If the layer is thinner than 0.8 times the median particle size, abrasion risk increases, and if the dimension is greater than 1.3 times, the magnitude assumed by the PET layer thickness by way of an increasing number of zeolite particles makes the migration of silver into the external median difficult to impossible. These particles are therefore ineffective and reduce the cost-effectiveness of the film.

Alongside the zeolites, further inorganic and/or organic particles can be present in the film. Examples of these calcium carbonate, amorphous silica, talc, magnesium carbonate, barium carbonate, calcium sulfate, barium sulfate, lithium phosphate, calcium phosphate, magnesium phosphate, aluminum oxide, lithium fluoride, the calcium, barium, zinc, or manganese salts of the dicarboxylic acids used, carbon black, titanium dioxide, kaolin, or crosslinked polymer particles, e.g. polystyrene particles or acrylate particles. The proportion of these particles in the antimicrobially modified layer(s) should not exceed 2000 ppm and is preferably below 1000 ppm. The only exception to this rule is provided by white film variants, but the median particle size of the white pigments (preferably $TiO_2$ or $BaSO_4$) used here should, at least in the antimicrobially modified layer, be below 1.8 μm, in order to avoid any excessive increase of surface roughness.

An outer layer having no antimicrobial modification preferably comprises at least 200 ppm of particles and particularly preferably at least 500 ppm, and preferably less than 2000 ppm, of particles.

In one preferred embodiment, the film also comprises at least one UV stabilizer. In principle, any of the organic and inorganic UV stabilizers suitable for incorporation in polyesters can be selected. These suitable UV stabilizers are known in the art and are described in more detail by way of example in U.S. Pat. No. 6,270,888 (whose WIPO equivalent is We 98/06575), U.S. Pat. No. 4,493,872 (whose European equivalent is EP-A-0 144 878), U.S. Pat. No. 4,347,350 (whose European equivalent is EP-A-0 031 202), U.S. Pat. No. 4,354,016 (whose European equivalent is EP-A-0 031 203), or U.S. Pat. No. 4,456,746 (whose European equivalent is EP-A-0 076 582). Examples of suitable compounds are 2-hydroxybenzophenones, 2-hydroxybenzotriazoles, organonickel compounds, salicylic esters, cinnamic ester derivatives, resorcinol monobenzoates, oxanilides, hydroxybenzoic esters, and sterically hindered amines, and/or triazines, preference being given to the triazines. That layer of the film which faces toward the light preferably comprises at least 50% more UV stabilizer (in % by weight) than the other layers, the total concentration of light stabilizer in the film preferably being in the range from 0.2% by weight to 5.0% by weight.

The addition of UV stabilizers prevents mechanical failure of the film over the course of time, in particular in outdoor applications. Alongside this, the UV stabilizer also reduces the increase in the yellowness index as the film ages. However, addition of silver-containing zeolite leads to a visible yellow to brown tinge even during the production process, and even without aging due to exposure to light. Alongside the light stabilizers, the film therefore preferably comprises at least one blue dye, to compensate for the yellow tinge triggered by the silver compound. It is preferable here to use dyes which are soluble in the polyester, rather than pigments, since if the latter are used the amount added has to be increased for the same effect, and these particles generate additional roughness. By way of example the following blue dyes can be used here: Clariant Blue RBL®, Blue RLS® (Ciba, CH); Lanxess (previously Bayer) Blue 3R® Gran, Blue RR® Gran (Lanxess, DE); Ciba FILESTER® type Blue GN (Ciba, CH). Alongside the blue dyes, it has also proven advantageous to add a green dye, such as IRGALITE® Green GFNP (Ciba SC, Basle, CH), in order to achieve a neutral color. The content of blue dye is preferably below 200 ppm in the film, and the proportion of green dye is preferably below 100 ppm. In the preferred embodiment, the yellowness index of the film is below 7, and particularly preferably below 3. Color stabilization is particularly important when the regrind arising during production is to be reused. It is advantageous to return a portion of the regrind to the antimicrobially modified outer layer. The proportion of regrind should not exceed 50% by weight in any layer, since higher proportions cause problems in running performance, because the zeolites are hygroscopic.

Alongside these stabilizers and dyes, the film can also comprise optical brighteners, such as Ciba TINOPAL® OB-One or others. However, this addition is less preferred than the addition of blue dye, since optical brighteners can function only in the presence of sufficient UV light.

The total thickness of the polyester film of the invention can vary widely. It is preferably from 8 to 500 μm, particularly preferably from 10 to 51 μm and very particularly preferably from 12 to 23 μm.

The film can moreover be coated on one or both sides. Alongside the usual functions of such coatings, e.g. for adhesion promotion, the coatings can also have a favorable effect on the antimicrobial properties of the film. Although it has been found that the acrylate coatings as described in U.S. Pat. No. 4,571,363 (whose European equivalent is EP-A-0 144 948) lower the initial antimicrobial activity of the film, they provide further opportunities for escape of silver, through abrasion of the coating over time, together with the cleaning cycles, and thus ensure that the film is effective for a longer period. Materials suitable for this purpose are not only crosslinking acrylates but in principle any of the coatings which in the finished state have no residual solubility in water, and examples here include silicone coatings, water-insoluble waxes, and polyesters. The thickness of the coating should be below 1 μm, preferably below 500 nm and particularly preferably below 350 nm, in order to ensure that the film has sufficient initial activity.

Alongside these coatings, it has proven advantageous for the coating to comprise non-migrating, intrinsically microbial components. Ammonium silanes of the following formula are particularly suitable:

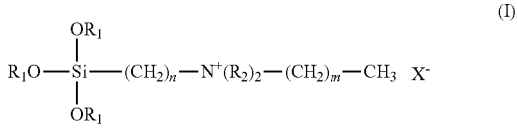

where
R₁ and R₂ are in each case identical or different and, independently of each other, are hydrogen moieties or C1-C8-alkyl moieties, which are straight-chain or—in the case of C3-C8-alkyl moieties—can be branched, R₁ and R₂ preferably being identical and being —CH₃; in aqueous dispersions, one, two or all of the R₁ moieties are hydrogen;
n is greater than 0 and smaller than 10, preferably from 2 to 5, and particularly preferably 3;
m is greater than 0 and smaller than 30, preferably from 6 to 25, and particularly preferably from 15 to 20, and very particularly preferably 17;
X⁻ is chloride, sulfate, or nitrate.

Examples of these compounds are available from Aegis (USA) or Sanitized (CH). They can be applied alone or else preferably with the abovementioned acrylate or with other coatings which are water-insoluble in the finished state.

These coatings can be produced either off-line or else preferably in-line (during polyester film production) by the known coating processes, preference being given to the "reverse gravure" process.

Production Process:

The invention also provides a process for the production of the polyester film of the invention, by the coextrusion process known from the literature.

The silver-containing zeolite is preferably introduced by way of a masterbatch into the corresponding layer. To this end, zeolite and polyester are mixed in a multiscrew extruder, extruded through a pelletizing die, and pelletized. U.S. Pat. No. 5,556,699 has previously indicated the requirements relating to the moisture level of the zeolite prior to masterbatch production. These requirements are also applicable in the present invention.

The procedure for the film production process is that the polymers corresponding to the individual layers, if appropriate inclusive of the additives, are melted in an extruder and coextruded through a flat-film die, the resultant prefilm is drawn off on one or more rolls for solidification, the prefilm is then biaxially stretched, and the biaxially stretched film is heat-set and then wound up.

The polymer for the antimicrobially modified outer layer (A) is preferably melted here in a twin-screw extruder, without prior drying. Prior drying, as would be necessary if a single-screw extruder were used, would cause an increase in the yellow tinge mentioned, by way of the additional thermal stress.

It is preferable that a temperature of 300° C. is not exceeded during extrusion, and it is particularly preferably that a temperature of 295° C., and ideally, in particular in the extruder for outer layer (A), that a temperature of 290° C. is not exceeded, since here again an excessive temperature leads to an increase in color tinge. However, on the other hand, extrusion temperatures should not be lower than 275° C., and ideally not lower than 280° C., since otherwise the size of individual zeolites can be reduced through the increase in shear.

The biaxial stretching (orientation) is generally carried out in succession, but can take place simultaneously, preference being given to sequential biaxial stretching, where stretching first takes place longitudinally (in machine direction) and then transversely (perpendicular to the machine direction). This leads to spatial orientation of the polymer chains. The longitudinal stretching can be carried out with the aid of two rolls rotating at different speeds corresponding to the desired stretching ratio. For the transverse stretching, an appropriate tenter frame is generally used, in which the film is clamped at the two edges and then drawn toward the two sides at an elevated temperature.

The temperature at which the stretching is carried out can vary relatively widely, and depends on the desired properties of the film. The longitudinal stretching is generally carried out at a temperature in the range of from 80 to 130° C., and the transverse stretching is generally carried out at a temperature in the range from 90 to 150° C. The longitudinal stretching ratio is generally in the range from 2.5:1 to 6:1, and in order to establish the desired mechanical properties (see below) it is preferably in the range from 3.0:1 to 5.5:1. The transverse stretching ratio is generally in the range from 3.0:1 to 5.0:1, and in order to establish the desired mechanical properties (see below) it is preferably in the range from 3.5:1 to 4.5:1.

In the heat-setting which follows, the film is kept for a period of from about 0.1 to 10 s at a temperature of from about 150 to 250° C. The film is then wound up conventionally.

The stated coatings are preferably applied to the film in-line by means of aqueous dispersions, prior to the transverse stretching step.

The modulus of elasticity of films produced by the abovementioned process, using the starting materials described, is greater than 2000 N/mm² in both directions of the film, preferably greater than 3000 N/mm², and particularly preferably greater than 3800 N/mm². These mechanical properties are advantageous for the use in the invention, since otherwise the film elongates too readily under mechanical load, and this can break the bond between matrix and zeolite and thus cause the particles to fall out of the film.

Advantages of the Invention

The film of the invention has very good effectiveness against bacteria. The action is moreover retained even after a number of cleaning cycles. The film is moreover easy to produce, and has little discoloration. In the sealable variant, it seals with respect to itself and with respect to substrates comprised of various polymers, such as polyamide, polycarbonate, and metals (e.g. aluminum, steel, lacquered steel, chromed or tin-coated steel). The film is therefore versatile. However, the film is also particularly suitable in non-sealable variants for application to metals and other substrates by the processes described in WO 2006/102858 A2 and WO 2006/102957 A2.

The raw materials for all of the layers of the film are in essence polyesters, and these permit recycling of the residues arising during production, and can give considerable cost savings through return into the silver-containing layer. The selection of raw materials also ensures that the antimicrobially modified layer cannot be washed off by water or by solvents conventionally used in the cleaning sector. The antimicrobially modified layer is also not sealable (i.e. tacky) at room temperature or at conventional processing temperatures (up to about 110° C.), thus having adequate resistance to damage. The antimicrobially modified layer is applied by coextrusion directly during base layer production, rather than in an expensive second step of a process, or indeed from solution, using solvents.

The films of the invention, and the items produced therefrom, are suitable by virtue of their excellent combinations of properties for a wide variety of different applications, for example for interior claddings, furniture cladding, air-conditioning systems, filter housings, medical equipment, walls of cold stores, medical packaging, food- or drink-packaging, applications in the sanitary sector, for hygiene items, wound plasters, applications in the apparel sector, and also film applications in greenhouses, etc.

The following test methods were used for the purposes of the present invention to characterize the raw materials and the films:

Measurement of Median Particle Diameter $D_{50}$ on Particles Prior to Introduction into the Raw Material:

Median particle diameter $d_{50}$ is determined by means of a laser on a MASTERSIZER® (Malvern Instruments, UK) by the standard method. Examples of other measurement equipment are HORIBA® LA 500 (Horiba Ltd., JP) or HELOS® (Sympatec GmbH, DE), which use the same measurement principle. For the test, the specimens are placed with water in a cell, and this is then placed in the measurement equipment. The measurement procedure is automatic and also includes mathematical determination of $d_{50}$. $d_{50}$ here is defined as determined as follows from the (relative) cumulative particle size distribution curve: the desired $d_{50}$ is given on the abscissa axis by the intersection of the 50% ordinate value with the cumulative curve.

Measurement of Median Particle Diameter $D_{50}$ on Zeolite Particles in the Film:

The film is introduced into a scanning electron microscope in such a way that the microbially modified side can be observed. On sections of size $100 \cdot 100$ $\mu m^2$, at 10 different sites on the surface, all of the zeolites >0.4 µm are measured and the median particle size for the sections is determined, and the average for the 10 sections gives the $d_{50}$ value for the particles in the film. The zeolites here can be identified on the basis of their characteristic shape or in the case of doubt by EDX elemental analysis.

The $d_{50}$ value is preferably measured on the (free, commercially available) particles used. If this is not possible, e.g. in the film itself or if the particles are already in finished masterbatch form when delivered, the method using counting in the film can also be selected. It is assumed here that the two test methods lead to identical results within the bounds of accuracy of measurement, and if non-aggressive production methods are used this is indeed the case. If the film producer is aware that, for example, because of high shear forces in the extruders, the median particle diameters in the film are deviating from those of the free, commercially available particles, a series of measurements in the film and standardization using particles with known $d_{50}$ value can be used to produce a correlation between the $d_{50}$ value of the free particles and the $d_{50}$ value of the particles in the film, thus permitting extrapolation from the data measured in the film to give the $d_{50}$ values in the free particles, and vice versa.

Measurement of Mechanical Properties of Film:

Mechanical properties are determined to DIN EN ISO 527-1 to 3.

Haze:

Haze is determined by a method based on ASTM D1003-52.

Roughness:

Roughness $R_a$ of the film is determined to DIN 4768.

Yellowness Index:

Yellowness index (YID) is the deviation from the colorless state in the "yellow" direction and is determined to DIN 6167.

Measurement of Antimicrobial Activity:

Antimicrobial activity is determined by a method based on JIS Z 2801, where antimicrobial activity is assessed as good if the number of *Escherichia coli* is reduced by at least 3 powers of ten, and as acceptable if a reduction by at least one power of ten is found.

Measurement of Antimicrobial Activity after Cleaning:

The film is wiped twice manually with a cotton cloth and then dried overnight in air. The cotton cloth here has been saturated with a mixture comprised of 99% of water and 1% of PRIL® (dishwashing liquid) from Henkel (DE). The film is then again wiped twice manually with a cotton cloth, and then again dried overnight in air. The cotton cloth here has been saturated with a mixture comprised of 95% of water and 5% of ethanol. Each of the two procedures is repeated 50 times. After this procedure, and after one day of waiting time at 25° C. and 50% rel. humidity, antimicrobial activity is determined as stated above.

Break-offs During Film Production:

The number of film break-offs per unit of time during production is compared with that during production of prior-art film and the percentage deviation is determined.

EXAMPLE 1

A three-layer film of thickness 20 µm was produced. The thickness of the antimicrobial outer layer (A) is 2.2 µm. The thickness of the sealable outer layer (C) is 2.0 µm. The thickness of the base layer (B) is 15.8 µm. The raw materials for each layer were separately melted in a twin-screw extruder, and were extruded through a three-layer flat-film die.

Raw materials MB1-5 comprise from 0.9 to 1.3% by weight of DEG; RT49 comprises 0.6% by weight of DEG; all of the raw materials mentioned (except S1) comprise <0.2% by weight of IPA and other diols and dicarboxylic acids at <0.1% by weight.

The raw materials added in the base layer (B) were as follows:

10% by weight of MB1=10% by weight of CYASORB® 1164 UV stabilizer (Cytec Inc., USA) and 90% by weight of polyethylene terephthalate (prepared by incorporating the UV stabilizer into the polyester in a twin-screw extruder)

90% by weight of RT49® polyethylene terephthalate from Invista (DE)

The raw materials used in the antimicrobially modified outer layer (A) were as follows:

20% by weight of MB1

20% by weight of MB2=10% by weight of AK80H silver-containing zeolite (Agion, USA) ($d_{50}$=2 µm; zeolite with 5% by weight of silver and 13% by weight of zinc) and 90% by weight of polyethylene terephthalate (prepared by incorporating the zeolite into the polyester in a twin-screw extruder)

60% by weight of RT49® polyethylene terephthalate from Invista (DE)

Raw Materials for Sealable Outer Layer (C):

97% by weight of S1, comprised of an amorphous copolyester having 80 mol % of ethylene terephthalate and 20 mol % of ethylene isophthalate (prepared by the trans-esterification process using Mn as transesterification catalyst: Mn concentration: 100 ppm)

3% by weight of MB3=10 000 ppm of $SiO_2$ particles (SYLYSIA® 320; producer Fuji Silysia, JP, with particle size $d_{50}$=2.5 µm) and 99% by weight of polyethylene terephthalate.

Coextrusion followed by stepwise longitudinal and transverse orientation was then used to produce a transparent, three-layer film with ABC structure.

The production conditions of the individual steps of the process were:

| Extrusion | Temperatures | A-layer | 281° C. |
| | | B-layer | 382° C. |
| | | C-layer | 285° C. |
| | Temperature of take-off roll | | 20° C. |
| Longitudinal stretching | Heating temperature | | 70-120° C. |
| | Stretching temperature | | 115° C. |
| | Longitudinal stretching ratio | | 3.7 |
| Transverse stretching | Heating temperature | | 100° C. |
| | Stretching temperature | | 125° C. |
| | Transverse stretching ratio | | 4 |
| Setting | Temperature | | 232° C. |
| | Duration | | 3 s |

Modulus of Elasticity
Longitudinal: 4500 N/mm$^2$
Transverse: 5100 N/mm$^2$
Yellowness index: 2.4
Roughness R$_a$: 200 nm
Antimicrobial Action
  Reduction in number of *Escherichia coli* after 24 h: 3.1 powers of ten
    after cleaning: reduction in number of *Escherichia coli* after 24 h: 2.8 powers of ten

EXAMPLE 2

A film was produced as described in Example 1, but the constitution of the antimicrobial outer layer was as follows:
20% by weight of MB1
20% by weight of MB2
25% by weight of S1
35% by weight of RT49
Modulus of Elasticity:
Longitudinal: 4450 N/mm$^2$
Transverse: 5060 N/mm$^2$
Yellowness index: 2.5
Antimicrobial Action
  Reduction in number of *Escherichia coli* after 24 h: 3.5 powers of ten
    after cleaning: reduction in number of *Escherichia coli* after 24 h: 3.3 powers of ten

EXAMPLE 3

A film was produced as described in Example 2, but the raw materials used in the base layer (B) were as follows:
8.5% by weight of MB1
20% by weight of regrind comprised of same material (recycled by means of a twin-screw extruder (max. temperature 285° C.) with subsequent pelletization)
71.5% by weight of RT49® polyethylene terephthalate from Invista (DE)
The constitution of the antimicrobial outer layer (A) was as follows:
13% by weight of MB1
18% by weight of MB2
17% by weight of S1
30% by weight of regrind comprised of same material
22% by weight of RT49
Modulus of Elasticity:
Longitudinal: 4300 N/mm$^2$
Transverse: 4950 N/mm$^2$
Yellowness index: 3.1
Antimicrobial Action
  Reduction in number of *Escherichia coli* after 24 h: 3.5 powers of ten
    after cleaning: reduction in number of *Escherichia coli* after 24 h: 3.2 powers of ten

EXAMPLE 4

A film was produced as described in Example 3, but the extrusion temperature in the extruder for the base layer and for the outer layer A was 295° C.
Modulus of Elasticity:
Longitudinal: 4300 N/mm$^2$
Transverse: 4950 N/mm$^2$
Yellowness index: 4.8
Antimicrobial Action
  Reduction in number of *Escherichia coli* after 24 h: 3.6 powers of ten
    after cleaning: reduction in number of *Escherichia coli* after 24 h: 3.2 powers of ten

EXAMPLE 5

A film was produced as described in Example 3, but the constitution of antimicrobial outer layer (A) was as follows:
13% by weight of MB1
18% by weight of MB2
17% by weight of S1
30% by weight of regrind comprised of same material
12% by weight of RT49
10% by weight of MB4 with 1% by weight of Ciba FILESTER® Blue GN and 0.1% by weight of IRGALITE® Green GFNP and 98.5% by weight of polyethylene terephthalate (DEG=0.9% by weight, other comonomers below 0.1% by weight)
Modulus of Elasticity:
Longitudinal: 4270 N/mm$^2$
Transverse: 4958 N/mm$^2$
Yellowness index: 0.6
Antimicrobial Action
  Reduction in number of *Escherichia coli* after 24 h: 3.5 powers of ten
    after cleaning: reduction in number of *Escherichia coli* after 24 h: 3.3 powers of ten

EXAMPLE 6

A film was produced as described in Example 1, but the constitution of the outer layer (C) was exactly the same as that of the antimicrobial outer layer (A). The thickness of the base layer was 15.6 µm.
Modulus of Elasticity:
Longitudinal: 4500 N/mm$^2$
Transverse: 5100 N/mm$^2$
Yellowness index: 3.7
Antimicrobial Action
  Reduction in number of *Escherichia coli* after 24 h: 3.2 powers of ten
    after cleaning: reduction in number of *Escherichia coli* after 24 h: 2.8 powers of ten

EXAMPLE 7

A film was produced as described in Example 1, but MB1 in the outer layer and base layer was replaced by RT49®.
Modulus of Elasticity:
Longitudinal: 4550 N/mm$^2$
Transverse: 5150 N/mm$^2$
Yellowness index: 1.7
Antimicrobial Action
  Reduction in number of *Escherichia coli* after 24 h: 3.2 powers of ten
    after cleaning: reduction in number of *Escherichia coli* after 24 h: 2.9 powers of ten

Comparative Example 1

A film was produced as described in Example 1, but MB2 was replaced by MB5.
MB5=10% by weight of silver-containing zeolite with $d_{50}$=0.5 μm, with 5% by weight of silver and 13% by weight of zinc, and 90% by weight of polyethylene terephthalate prepared as described in U.S. Pat. No. 5,556,699. Masterbatch prepared by incorporation of the zeolite into the polyester in a twin-screw extruder.
Modulus of Elasticity:
Longitudinal: 4480 N/mm$^2$
Transverse: 5130 N/mm$^2$
Yellowness index: 2.5
Antimicrobial Action
  Reduction in number of *Escherichia coli* after 24 h: 3.3 powers of ten
    after cleaning: reduction in number of *Escherichia coli* after 24 h: 1.6 powers of ten

Comparative Example 2

A film was produced as described in Example 1, but the thickness of the antimicrobial outer layer was 9 μm and that of the base layer was 9 μm.

Although good initial activity values were found, with a reduction by 3.2 powers of ten, and also good values after cleaning, with a reduction by 2.9 powers of ten, the content of expensive silver zeolite, higher by a factor of more than 3, exhibited no significant improvement of action.
Modulus of Elasticity:
Longitudinal: 4490 N/mm$^2$
Transverse: 5090 N/mm$^2$
Yellowness index: 6.8
Antimicrobial Action
  Reduction in number of *Escherichia coli* after 24 h: 3.4 powers of ten
    after cleaning: reduction in number of *Escherichia coli* after 24 h: 2.9 powers of ten

Comparative Example 3

Example 2 of WO 2006/000755 was repeated.
Antimicrobial Action
  Reduction in number of *Escherichia coli* after 24 h: 1.6 powers of ten
    after cleaning: reduction in number of *Escherichia coli* after 24 h: 0.8 powers of ten.

All references cited herein are hereby incorporated by reference in their entirety.

That which is claimed:

1. An at least two-layer polyester film comprising at least one antimicrobially modified outer layer (A), wherein the antimicrobially modified outer layer (A) comprises
    a) from 1 to 6% by weight of a silver-loaded zeolite, based on the weight of the outer layer (A),
    b1) a layer thickness <8 μm, and
    b2) the layer thickness is not greater than 1.3 times the median particle size of the zeolite,
    wherein the median particle size ($d_{50}$) of the silver-loaded zeolite is from 0.5 to 6 μm, and the surface roughness, Ra, of outer layer (A) is below 1000 nm, as determined via DIN 4768.

2. An at least two-layer polyester film as claimed in claim 1 comprising at least one antimicrobially modified outer layer (A), wherein the antimicrobially modified outer layer (A) comprises
    a) from 1 to 6% by weight of a silver-loaded zeolite, based on the weight of the outer layer (A),
    b1) a layer thickness <8 μm, and
    b2) the layer thickness is not greater than 1.3 times the median particle size of the zeolite,
    wherein the median particle size ($d_{50}$) of the silver-loaded zeolite is from 0.5 to 6 μm, the modulus of elasticity for the film is greater than 3800 N/mm$^2$.

3. The polyester film as claimed in claim 1, wherein the amount of silver in the zeolite is from 0.5 to 20% by weight, based on the weight of the zeolite.

4. The polyester film as claimed in claim 1, wherein the zeolite comprises from 1 to 20% by weight of zinc and/or copper, based on the weight of the zeolite.

5. The polyester film as claimed in claim 1, wherein the thickness of the outer layer (A) is from 0.75 to less than 8 μm.

6. The polyester film as claimed in claim 1, said film comprising further inorganic and/or organic particles, alongside the zeolite.

7. The polyester film as claimed in claim 1, said film comprising a further outer layer (C).

8. The polyester film as claimed in claim 7, wherein the outer layer (C) comprises at least 200 ppm of particles, based on the weight of the outer layer (C).

9. The polyester film as claimed in claim 1, wherein said film further comprises at least one UV stabilizer.

10. The polyester film as claimed in claim 9, wherein the UV stabilizer is a triazine.

11. The polyester film as claimed in claim 9, wherein the layer facing toward light, for an intended application of the film, comprises at least 50% more UV stabilizer (in % by weight) than the other layers.

12. The polyester film as claimed in claim 9, wherein the total concentration of UV stabilizer is in the range from 0.2% by weight to 5.0% by weight.

13. The polyester film as claimed in claim 1, wherein said film comprises at least one dye which is soluble in the polyester.

14. The polyester film as claimed in claim 1, wherein the total thickness of said film is from 8 to 500 μm.

15. The polyester film as claimed in claim 1, wherein said film comprises coating on one or both sides.

16. A process for producing a film as claimed in claim 1, said process comprising
    a) melting polymers corresponding to the individual layers in an extruder and
    b) coextruding the layers through a flat-film die,
    c) drawing off the resultant prefilm for solidification on one or more rolls,
    d) biaxially stretching the prefilm, and e) heat-setting the biaxially stretched film and f) taking up the heat-set film, wherein said process further comprises i) introducing from 1 to 6% by weight of a silver-loaded zeolite in the polymer of the outer layer (A), and ii) extruding the outer layer (A) at a thickness that, after biaxial orientation and heat-setting, provides a layer thickness of <8 μm, and that further is not greater than 1.3 times the median particle size of the zeolite.

17. Interior cladding, furniture cladding, air-conditioning systems, filter housings, medical equipment, cold stores, refrigerators, medical packaging, food- or-drink packaging, sanitary sector applications, hygiene items, wound plasters, apparel, or greenhouses comprising film as claimed in claim 1.

18. The polyester film as claimed in claim 1, wherein the antimicrobially modified outer layer (A) comprises from 60 to less than 99 mol % of ethylene glycol units and terephthalic acid units and one or more copolyester components selected from (i) from 1 to 10% by weight of isophthalic acid units; (ii) from 1 to 10% by weight of diethylene glycol units; (iii) from 0.7 to 10% by weight of other diol units; (iv) from 1 to 10% by weight of dicarboxylic acid units other than terephthalic acid, and the concentration of the silver-loaded zeolite in the outer layer (A) is from 1 to 6% by weight.

19. An at least two-layer polyester film comprising at least one antimicrobially modified outer layer (A), said antimicrobially modified outer layer (A) comprising a) from 0.5 to 15% by weight of a silver-loaded zeolite, based on the weight of the outer layer (A), b1) a layer thickness <8 μm, and b2) the layer thickness is not greater than 1.3 times the median particle size of the zeolite, wherein the median particle size ($d_{50}$) of the silver-loaded zeolite is from 0.5 to 6 μm, the modulus of elasticity for the film is greater than 3800 N/mm², and the antimicrobially modified outer layer (A) comprises first and second sized silver-loaded zeolite particles, said first particles ranging in size from 1.8 to 6 microns and said second particles ranging in size from greater than or equal to 0.5 microns to less than 1.8 microns, said second particles present in an amount ranging from 20 to 60% by weight of the first silver-loaded zeolite particles.

* * * * *